: (12) United States Patent
Ribak

(10) Patent No.: US 7,708,402 B2
(45) Date of Patent: May 4, 2010

(54) GOGGLES FOR IMPROVED OCULAR VISION

(75) Inventor: Erez Ribak, Haifa (IL)

(73) Assignee: Technion Research and Development Foundation Ltd., Haifa (IL)

(*) Notice: Subject to any disclaimer, the term of this patent is extended or adjusted under 35 U.S.C. 154(b) by 282 days.

(21) Appl. No.: 11/630,272

(22) PCT Filed: Jun. 23, 2005

(86) PCT No.: PCT/IL2005/000676

§ 371 (c)(1),
(2), (4) Date: Dec. 26, 2007

(87) PCT Pub. No.: WO2006/001013

PCT Pub. Date: Jan. 5, 2006

(65) Prior Publication Data

US 2008/0218685 A1    Sep. 11, 2008

Related U.S. Application Data

(60) Provisional application No. 60/582,431, filed on Jun. 25, 2004.

(51) Int. Cl.
*G02C 7/04* (2006.01)
(52) U.S. Cl. .................................................. 351/160 R
(58) Field of Classification Search ................. 351/158, 351/118, 160 R, 161, 177, 200, 205, 206, 351/212, 219, 221, 247; 623/6.11, 6.34, 623/6.37, 6.44, 6.46; 2/15; 128/858; 604/20
See application file for complete search history.

(56) References Cited

U.S. PATENT DOCUMENTS 1,528,192 A    3/1925   Brierton
3,542,461 A *  11/1970  Sampson et al. ........ 351/160 R
4,396,261 A    8/1983   Herbert (Continued)

OTHER PUBLICATIONS

Young Thomas, "The Bakerian Lecture. On the mechanism of the eye", Philosophical Transactions of the Royal Society of London, vol. 91, pp. 23-88, Nov. 27, 1800.

(Continued)

*Primary Examiner*—Loha Ben
(74) *Attorney, Agent, or Firm*—Pearl Cohen Zedek Latzer, LLP

(57) ABSTRACT

A device for improved vision into or out of at least one eye of a subject. The device comprises an enclosing vessel for holding one or more lenses in front one or two eyes of the subject and for holding a substance whose refractive index is matched to the refractive index of the cornea. The vessel is adapted to seal the substance to the face around the eye or eyes of the subject thereby allowing focusing into or out of the eye or eyes.

24 Claims, 6 Drawing Sheets

U.S. PATENT DOCUMENTS

| | | | |
|---|---|---|---|
| 4,890,903 A | | 1/1990 | Treisman et al. |
| 5,347,326 A | * | 9/1994 | Volk .................. 351/160 R |
| 5,521,657 A | | 5/1996 | Klopotek |
| 5,537,164 A | | 7/1996 | Smith |
| 5,548,352 A | * | 8/1996 | Dewey .................. 351/160 H |
| 5,706,073 A | * | 1/1998 | Volk .................. 351/219 |
| 5,776,068 A | | 7/1998 | Silverman et al. |
| 5,777,719 A | | 7/1998 | Williams et al. |
| 5,927,281 A | | 7/1999 | Monteleone et al. |
| 6,248,732 B1 | * | 6/2001 | Itoh et al. .................. 514/167 |
| 6,394,999 B1 | | 5/2002 | Williams et al. |
| 6,458,108 B1 | | 10/2002 | Tangri |
| 6,478,792 B1 | * | 11/2002 | Hansel .................. 606/5 |
| 6,618,208 B1 | | 9/2003 | Silver |
| 2004/0056986 A1 | | 3/2004 | Blum et al. |

OTHER PUBLICATIONS

Milodot Michel et al., "Contribution of the cornea and lens to the spherical aberration of the eye", Vision Research, vol. 19, pp. 685-687, 1979.

Artal Pablo et al., "Compensation of corneal aberrations by the internal optics in the human eye", Journal of Vision, vol. 1, pp. 1-8, May 1, 2001.

Hway-Lan Liou et al., "Anatomically accurate, finite model eye for optical modeling", Journal of the Optical Society of America, A, vol. 14, No. 8, pp. 1684-1695, Aug. 8, 1997.

International Search Report of Application No. PCT/IL05/00676 Mailed on Nov. 28, 2006.

* cited by examiner

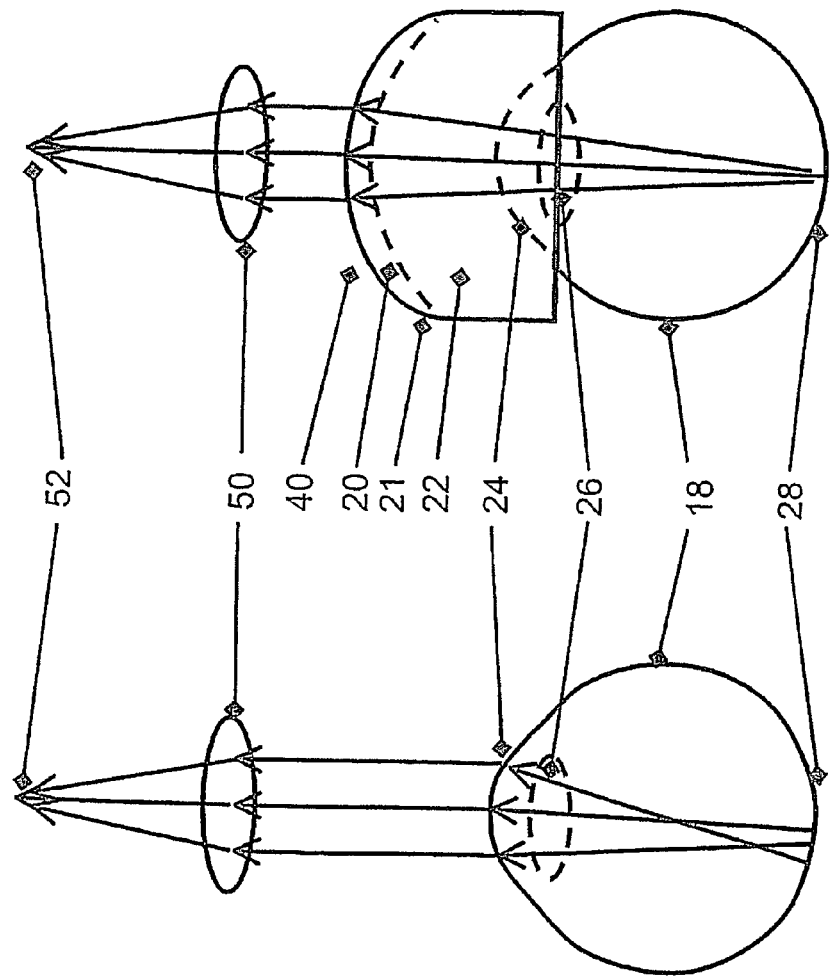

GOGGLES FOR IMPROVED OCULAR VISION

CROSS-REFERENCE TO RELATED APPLICATIONS

This application is a National Phase Application of PCT International Application No. PCT/IL2005/000676, entitled "Goggles for improved Ocular Vision", International Filing Date Jun. 23, 2005, published on Jan. 5, 2006 as International Publication No. WO 2006/001013, which in turn claims priority from U.S. Provisional Patent Application No. 60/582, 431, filed Jun. 25, 2004, both of which are incorporated herein by reference in their entirety.

FIELD OF THE INVENTION

The present invention relates to improved ocular vision devices, methods of their fabrication, implementations and uses thereof. Specifically, the present invention relates to liquid filled goggles whose front lens (or window) is designed to focus into the eye and out of it, while the immersion substance nulls or reduces aberrations of the cornea.

BACKGROUND OF THE INVENTION

Optical aberrations can impede a person's vision and interfere with diagnostic and medical procedures. Most optical aberrations occur in the cornea and the tear film, with additional contribution from the crystalline lens and marginally from the ocular humours. In the case of dilated pupils, the actual focus spot size on the retina is in the range of 20-100 micrometers, instead of the theoretical range of 1-2 micrometers. This blurs severely the details available to the eye. In addition, the tear film and crystalline lens vary with time, further affecting the spot size.

In addition to affecting a person's eyesight, poor optical conditions can also reduce the effectiveness of eye examinations and treatment. An ophthalmologist examining the eye is restricted to details no finer than the focus spot size. This significantly limits his or her ability to locate early warning signs of abnormalities, diagnose ocular diseases, or perform follow-ups on eye operations. Corneal aberrations also interfere in the examination and treatment of other parts of the eye, such as the aqueous humour and the crystalline lens.

An eye surgeon applying a laser beam to the retina to treat the eye is limited by optical aberrations which result in a large beam spot, thereby causing neighboring areas of the retina to be heated and unnecessarily damaged. And, because of limitations on his or her own view, the surgeon might not even be aware of these damages. These aberrations in the cornea are somewhat reduced by the use of a contact lens attached to the eye with an intervening immersion gel. The device also keeps the lids open during the surgery, but it causes great inconvenience to the patient.

It would therefore be beneficial to have a solution for overcoming the deleterious effects of corneal aberrations on vision, diagnosis, and treatment.

One set of prior art solutions employs some form of scanning in one, two or three dimensions, which enables sequential separation and measurement of the details. This group includes the scanning slit lamp, the scanning laser ophthalmoscope, optical coherence tomography, and acoustic imaging, among others. The optically measuring devices suffer less from the aberrations, but have a limited resolution nevertheless. Another powerful method is adaptive optics, where correction for the ocular aberrations is performed in a servo loop. This method allows direct imaging of the interior of the eye, and in combination with other methods such as mentioned here, even finer scanning of details. It is described by Williams and Liang in U.S. Pat. No. 5,777,719, "METHOD AND APPARATUS FOR IMPROVING VISION AND THE RESOLUTION OF RETINAL IMAGES". A similar solution for laser surgery is described in U.S. Pat. No. 6,394,999, "LASER EYE SURGERY SYSTEM USING WAVEFRONT SENSOR ANALYSIS TO CONTROL DIGITAL MICROMIRROR DEVICE (DMD) MIRROR PATTERNS" by Williams et al. Unfortunately, all of these methods are rather complicated and the instrumentation takes up large volume. The equipment used is cumbersome, expensive, and many parts of the technology are still immature.

When high resolution is not essential, it is possible to trade it for a very large field. Goniometric devices such as the Abraham or Goldmann objectives were devised in order to gain access to up to 180 degrees in the eye, using up to four mirrors. But the price to be paid is a loss of magnification, and even demagnification of the observed—or laser treated—portions of the retina or the iris. These objectives are placed on the anaesthetized cornea using an immersion gel or fluid, such as methyl cellulose.

A number of prior art references refer to the use of filled goggles. It should be noted that in the context of this disclosure, the word "goggles" refers to a device worn over one or both eyes and comprising an enclosed volume, sealed to the face, which can be filled with a medium such as a liquid or gel, thereby covering all of the eye with the medium. Herbert, in U.S. Pat. No. 4,429,956, "WET CORNEA TELESCOPE", describes a telescope that has a fluid-filled cell all the way to the cornea for improved optical quality. Herbert (again), in U.S. Pat. No. 4,396,261, "METHOD FOR DETERMINING THE CURVATURE OF A CORNEA", suggests the use of flat goggles filled with fluid for measurement and calculations for fitting contact lenses. Silverman et al., U.S. Pat. No. 5,776, 068, "ULTRASONIC SCANNING OF THE EYE USING A STATIONARY TRANSDUCER", describe an ultrasonic scanner for the eye, which is attached to liquid-filled goggles for better acoustic contact. Monteleone and Monteleone describe in U.S. Pat. No. 5,927,281, "GOGGLES FOR PREVENTING EXPOSURE KERATITIS", fluid-filled goggles for maintaining proper environment for eyes with corneal keratitis.

Thomas Young, "On the mechanism of the eye", Philosophical Transactions of the Royal Society of London vol. 91, 23-88, 1801, and later M. Milodot and J. Sivak, "Contribution of the cornea and the lens to the spherical aberration of the eye", Vision Research vol. 19, 685-687, 1979, and then P. Artal et al., "Compensation of corneal aberrations by the internal optics in the human eye", Journal of Vision 1, 1-8, 2001, all show how liquid-filled flat goggles gloss over corneal aberrations in order to separate the optical functions of the cornea and crystalline lens. The largest disadvantage of this method is the need to add very strong positive lenses next to the flat goggles. This is required to further compensate the tens of dioptres of optical power in the cornea itself, lost by its immersion in the fluid. Without this external compensation, the magnifying power of the eye is lost, both for the person wearing the goggles and for the doctor looking into the eye, or operating on it.

It is a main object of the present invention to provide goggles filled with a substance whose refractive index is matched to the refractive index of the cornea, thus reducing the effects of corneal aberrations and tear film variations and improving ocular vision.

Other objects and advantages of the present invention will become apparent after reading the present specification and reviewing the accompanying drawings.

BRIEF DESCRIPTION OF THE INVENTION

There is thus provided, in accordance with some preferred embodiments of the present invention, a device for improved vision into or out of at least one eye of a subject, the device comprising:

at least one enclosing vessel for holding at least one lens in front of at least one eye of the subject and for holding a substance whose refractive index is matched to the refractive index of the cornea, wherein the vessel is adapted to seal the substance to the face around said at least one eye of the subject;

thereby allowing focusing into or out of said at least one eye or both.

Furthermore, in accordance with some preferred embodiments of the present invention, the device is provided with at least one strap for restraining the device on the face of the subject.

Furthermore, in accordance with some preferred embodiments of the present invention, said at least one enclosing vessel comprises two vessels, each vessel provided with a lens.

Furthermore, in accordance with some preferred embodiments of the present invention, the device is incorporated in a helmet provided with at least one restraining strap.

Furthermore, in accordance with some preferred embodiments of the present invention, the device is provided with an adapter for attaching the device to a separate device.

Furthermore, in accordance with some preferred embodiments of the present invention, the optical properties of the lens are variable.

Furthermore, in accordance with some preferred embodiments of the present invention, the device is further provided with at least one external optical element placed in front of the device and whose optical properties are variable.

Furthermore, in accordance with some preferred embodiments of the present invention, said at least one lens is selected from a group of optical systems consisting of a single lens, a doublet, a triplet, a diffractive lens, a variable index lens a compound lens, flexible lens, lens with anti-reflection coating, mirrors, or a combination thereof.

Furthermore, in accordance with some preferred embodiments of the present invention, the device is provided with an adjustment mechanism for orienting and displacing said at least one lens.

Furthermore, in accordance with some preferred embodiments of the present invention, the vessel has at least one opening in it through which the substance can be changed or modified or added or removed.

Furthermore, in accordance with some preferred embodiments of the present invention, the device is further provided with at least one transparent partition so as to allow the vessel to separately hold substances of different optical characteristics.

Furthermore, in accordance with some preferred embodiments of the present invention, the device is further provided with a light source for illuminating said at least one eye.

Furthermore, in accordance with some preferred embodiments of the present invention, the device is provided with at least one wave guide for guiding light into said at least one eye.

Furthermore, in accordance with some preferred embodiments of the present invention, the vessel is flexible.

Furthermore, in accordance with some preferred embodiments of the present invention, there is provided a method for improving vision into or out of at least one eye of a subject, the method comprising:

providing a device comprising at least one enclosing vessel for holding at least one lens in front of at least one eye of the subject;

providing within the vessel at least one substance whose refractive index is matched to the refractive index of the cornea, sealing the vessel to the face around said at least one eye of the subject; thereby allowing focusing into or out of said at least one eye or both.

Furthermore, in accordance with some preferred embodiments of the present invention, the method further comprises strapping the vessel to the face of the subject.

Furthermore, in accordance with some preferred embodiments of the present invention, the method further comprises displacing or tilting said at least one lens.

Furthermore, in accordance with some preferred embodiments of the present invention, the method further comprises placing one or more transparent substances separately in the vessel.

Furthermore, in accordance with some preferred embodiments of the present invention, the method further comprises changing pressure within the vessel to change at least one optical property of the device.

Furthermore, in accordance with some preferred embodiments of the present invention, matching the refractive index of the substance to the refractive index of the cornea comprises partially or fully replacing or mixing the substance within the vessel with another substance of different optical properties or for nutritional or medical purposes.

Furthermore, in accordance with some preferred embodiments of the present invention, the method further comprises applying pressure on or around said at least one lens to change its optical properties.

Furthermore, in accordance with some preferred embodiments of the present invention, the method is used in conjunction with ocular measurements or imaging.

Furthermore, in accordance with some preferred embodiments of the present invention, the method is used in conjunction with ocular surgery or procedure.

Furthermore, in accordance with some preferred embodiments of the present invention, the method further comprises correcting further aberrations using an adaptive optics system, the system comprising at least one component from a group of components consisting of a wave front sensor, a wave front modulator, and a servo controller.

BRIEF DESCRIPTION OF THE FIGURES

The invention is described herein, by way of example only, with reference to the accompanying Figures, in which like components are designated by like reference numerals. In order to reduce confusion, the heads of arrows signifying light rays have open heads, and arrows pointing instrumental details were given a filled square head style.

FIG. 2a is a schematic drawing showing a sectional view of the eye of a subject with a poor cornea with light reflecting out from the retina into an external optical device, where at the device focus arrive beams from different retinal positions.

FIG. 2b illustrates the same light passage as in FIG. 2a with the addition of goggles in accordance with a preferred embodiment of the present invention, where now the external focus images a finer retinal spot.

DETAILED DESCRIPTION OF THE INVENTION

Figures 1A, 1B:
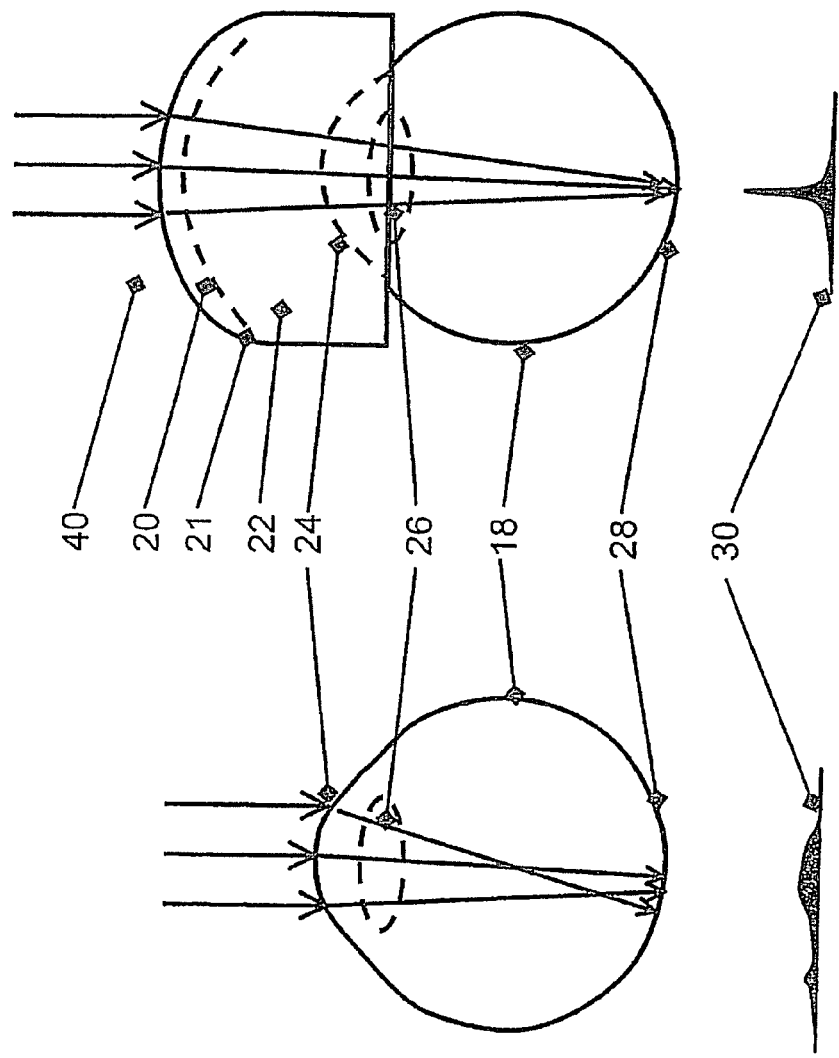
FIG. 1a is a schematic drawing showing a sectional view of the eye of a subject with a poor cornea with a light beam entering and forming a fuzzy image on his retina.
FIG. 1b illustrates the same light mechanism as in FIG. 1a with the addition of goggles in accordance with a preferred embodiment of the present invention, thereby sharpening the image on the retina.

The present invention provides a solution to reduced vision acuity caused by aberrations in the cornea and the tear film. The invention comprises goggles filled with a substance having a refractive index matched to the refractive index of the cornea and worn over one or both eyes. The front window or lens of the goggles is perfected in order to allow high resolution vision both into the eye and out of it.

The goggles of the present invention have many uses in the field of ophthalmology. Principal uses include:
  Subjects with impaired vision can wear the goggles as eyeglasses, thereby improving their focus.
  Ophthalmologists and health care technicians can have their patients wear the goggles, thereby improving the focus spot size for examinations. The patient can wear the goggles alone or integrated into the examination apparatus, for example, as part of the head restraint or the front end of a fundus camera.
  Eye surgeons can have their patients wear the goggles, thereby improving the focus spot size for more accurate treatment, such as laser surgery.

In additions, subjects wishing to improve their eyesight for a limited time, or in order to carry on special tasks requiring high resolution, may gain by wearing the goggles.

Before explaining at least one embodiment of the invention in detail, it is to be understood that the invention is not limited in its application to the details of construction, arrangement and the utilization of the components set forth in the following description or illustrated in the drawings. The invention is readily capable of being implemented in other embodiments or of being practiced or carried out in various ways. Also, it is to be understood that the phraseology and terminology employed herein is for the purpose of description and should not be regarded as limiting.

The present invention circumvents optical degradation by the surface of the cornea and the tear film, by providing an external artificial cornea, with the space between it and the natural cornea filled with substance having a refractive index equal or closely matched to that of the natural cornea. This equality of indices nulls the corneal optical deviations, and only internal variations of the refractive index inside the eye might still contribute to other aberrations. These internal variations are mostly caused by the crystalline lens, but may also arise from the aqueous and vitreous humours, and are usually much weaker.

Once adjusted, the goggles create a standard eye of constant length, no matter what the original eye length was, hence significantly reducing adjustment requirements from the rest of the measurement or surgery devices, be it optical coherence tomography, scanning laser ophthalmology, fundus cameras, lasers, etc.

Another advantage of the goggles, in addition to circumventing corneal degradation, is that they fully compensate for the otherwise disturbing effect of the variable tear film. Thus, the material, quality and shape of the goggles become the main factor in the quality of images of the retina, of the incident laser spot size, or of the visual acuity of the observer wearing the goggles.

FIG. 1a is a top view generalized schematic drawing of light entering the eye 18 of a patient with a poor cornea. The figure can also serve to illustrate a beam entering the eye during laser surgery. FIG. 1a shows that a wide beam entering the eye is refracted into different directions by aberrated cornea 24, passing through lens 26 to hit retina 28 with a wide light distribution as shown by intensity profile 30.

FIG. 1b illustrates the same light mechanism as in FIG. 1a with the addition of the goggles 40 of the present invention. The wide beam passes first through lens 20, then immersion substance 22, which is held in cup 21. The effect of aberrating cornea 24 is not significant since its index of refraction is matched to the refractive index of the immersion substance 22 before it. Therefore the retinal light distribution is now much tighter, as shown in profile 30.

FIGS. 2a and 2b illustrate the same views as those of FIGS. 1a and 1b respectively but showing the path of light reflecting out from retina 28, as perceived by a medical professional or device forming an image of the retina.

In FIG. 2a, light beams arriving from different points on retina 28 and diffracting through different parts of the aberrated cornea 24 is focused into a single spot 52 leading to a blurred image in optical system 50. Thus the idea of a perfect optical system where only one object point is relayed into one image point is not realized. In FIG. 2b, filled goggles 40 mask away the effect of corneal 24 aberrations and each image point in the optical system receives light from a single retinal point.

Optical system 50 is drawn schematically as a lens focusing onto a point 52, but it is usually more complicated, having a multiplicity of light sources, mirrors, lenses, scanners, filters, beam splitters, detectors and the like. A very simple optical system could be the doctor's eye, where thanks to the goggles on the patient, he can now see much finer details on the patient's retina.

Imaging is described here of the retina proper, but finer focusing is also possible on other features of the eye, such as inhomogeneities in the crystalline lens or the vitreous humour. Also possible is focusing on shallower or deeper parts of the retina, for example ganglion cells or blood vessels, or focusing on the periphery of the retina, the fovea or the macula. Nearer by, other parts of the eye, such as the cornea, iris, crystalline lens or the aqueous and vitreous humours can be brought into sharper focus. Focusing into different depths of the eye are achieved in general by optical system 50, and the object or target of the beams in the figures can also be all the way out to the cornea, even if not marked so.

In an alternative embodiment of the present invention, the refractive index of substance 22 can differ from that of cornea 24. Broken lines in FIGS. 1 and 2 represent a change of refractive index of lesser importance than that from air (refractive index 1.00) to cornea 24 (refractive index 1.37). For example between 1.34 for a filler substance 22 comprising saline solution and 1.37 for cornea 24, and similarly between crystalline lens 26 (index 1.38) and the aqueous and vitreous humours (index 1.34), which fill up the rest of eye 18.

Figure 6:
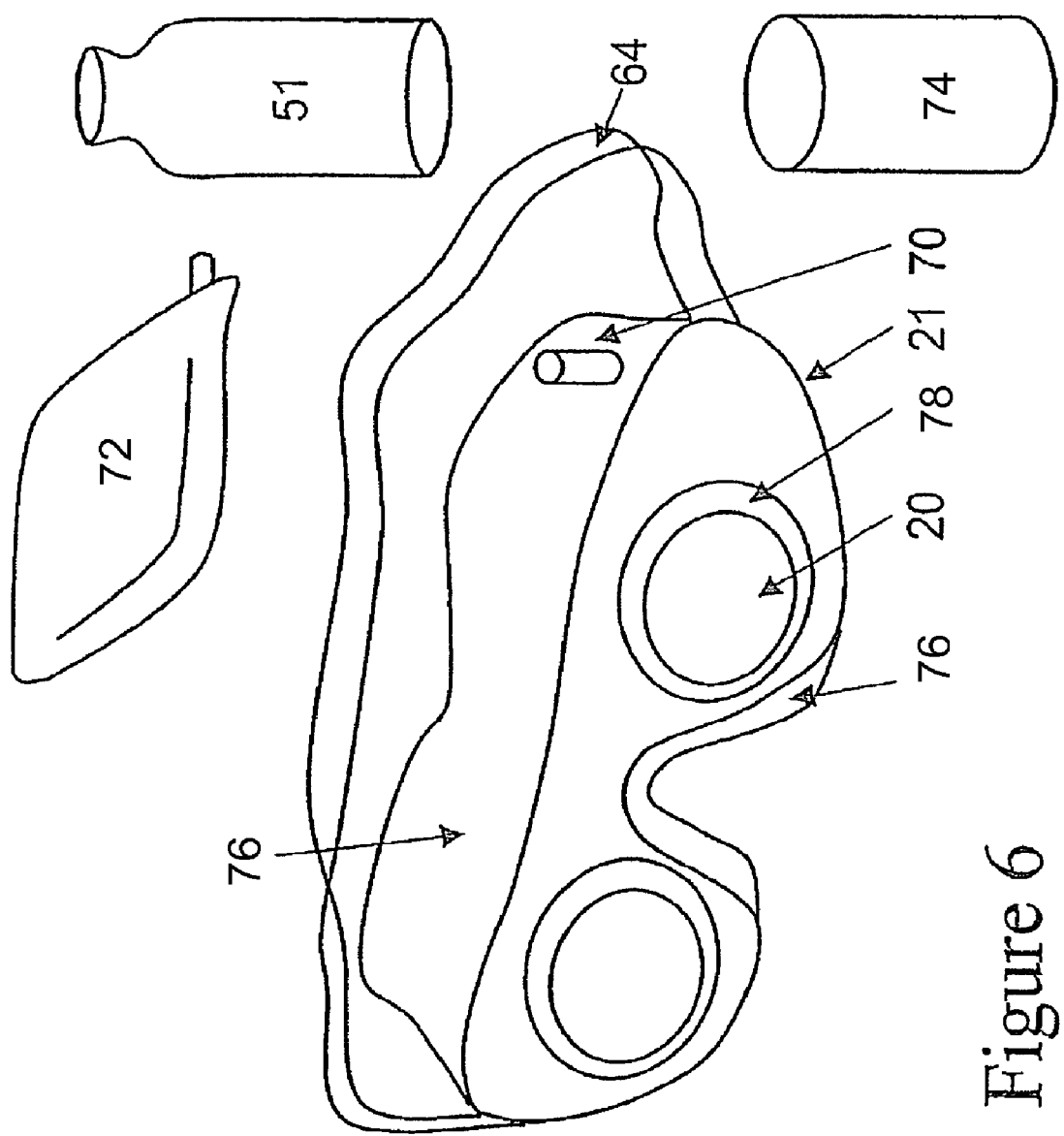
FIG. 6 is a side view schematic illustration of exemplary goggles which allow sealing to the wearer's face, adjusting the lens position, and modifying the necessary fluid content in the goggles, in accordance with a preferred embodiment of the present invention.

Goggles 40 can be implemented in various formats, for example, as a single cup 21 for placement over one eye of a subject; as two cups, one placed over each eye; or as a facemask type of implementation covering both eyes. In the case of a face-mask implementation, the face mask itself can serve as a single cup 21 covering both eyes as shown in FIG. 6. Alternatively, it can serve as a holder for one cup 21 covering one eye or for two cups, each covering one eye. The subject wearing the single goggle, the two goggles, or the mask, can be a person or an animal.

Figure 3:
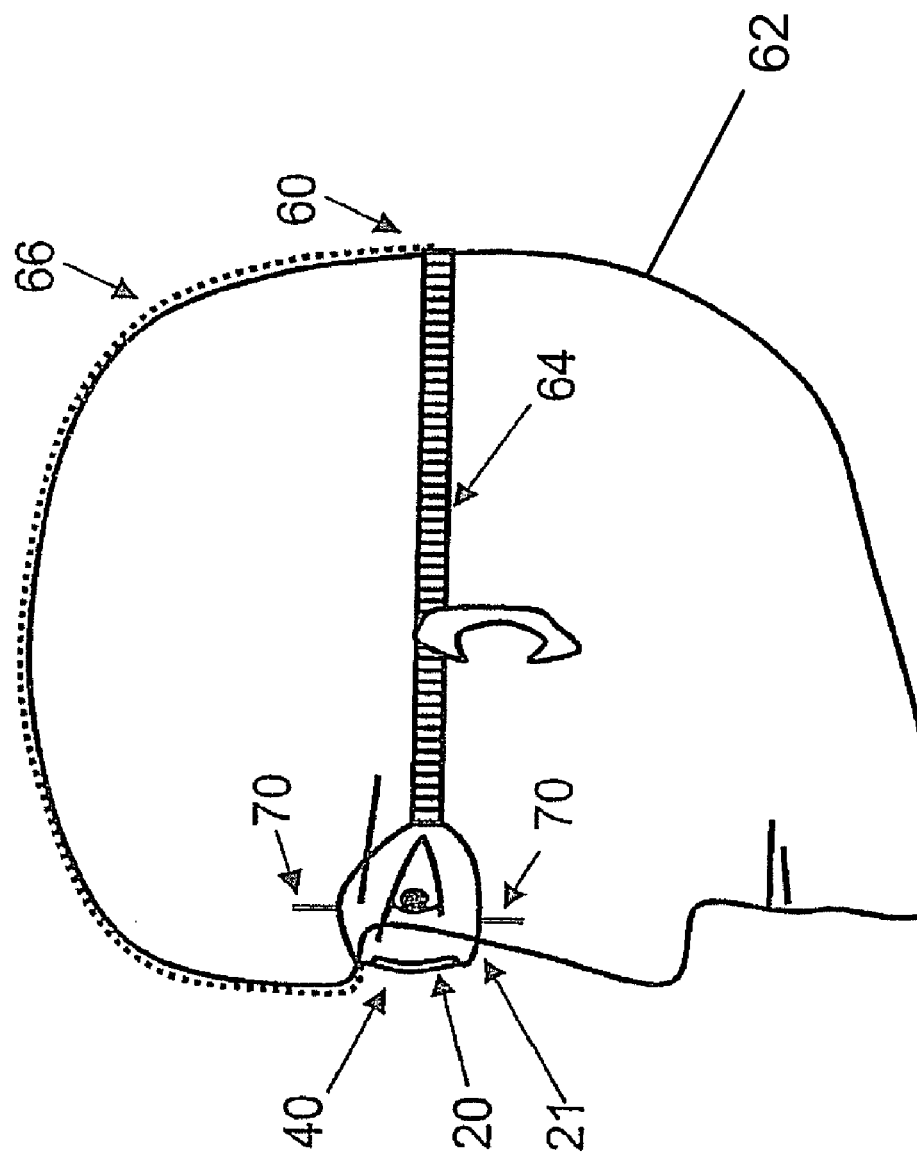
FIG. 3 is a side view schematic drawing of a retaining arrangement for retaining goggles on a subject in accordance with a preferred embodiment of the present invention.

FIG. 3 is a side view schematic drawing of a restraining arrangement 60 for retaining goggles 40 on a subject 62. Restraining arrangement 60 comprises adjustable straps between the eyes, strap 64 around the head and optionally top strap 66 over the top of the head, to enable accurate placement and retention of the centers of goggle 40 cups against the eyes 18. Top strap 66 might be necessary for heavier goggles. Even more straps or even a helmet might be needed for more complex goggles.

Where accurate positioning is beneficial, the goggles can be a part of another optical device such as an ophthalmoscope or laser. In that case the head of the subject is held against the goggles in order to seal them, and restraining straps or helmet might have a secondary role. Accurate positioning is of the whole head is a part of prior art, and includes, among others, a brow rest, a chin rest, a bite bar, or a combination thereof.

Immersion substance 22 comprises a fluid, a liquid, a gel, or other soft material and is either previously present in cup 21 or is added through filling lines 70 until no significant air bubbles remain between front lens 20 and cornea 24. The amount, position, and size of the remaining bubbles is kept minimal so that it does not disturb the optical path into or out of the eye, as would be obvious to persons skilled in the art. Unlike in prior art, it is not required for the optics to be in contact or near contact with cornea 24. Rather, the goggle of the present invention is sealed to the face around the eye, rendering this configuration friendlier or less irritating for the subject wearing it.

Different persons might prefer to have the goggles filled with their eyes closed and then open them, while others might choose to have the goggles filled with their eyes open. For convenience, filler substance 22 should have an acidity (Ph) that does not disturb the subject or irritate the eye. For example, a saline solution of 0.9% NaCl, artificial tears, or methyl cellulose. At the same time, immersion substance 22 should have an index of refraction as close as possible to that of the cornea, to minimize the effect of corneal aberrations, and can be chosen from a group containing sugar water, saline solution, methyl cellulose, and other substances.

FIG. 6 displays a face mask 40 with sealing edges 76 at the periphery around the eyes, a head strap 64, and filling line 70. Different mechanisms can be used for filling and draining the goggles, such as by a retractable syringe, with or without valves, to avoid spillage. Filling and draining tubes leading from and to one or more reservoirs are another option. The immersion material can be added from a group containing a bottle 51, bag 72, syringe, and the drainage can be into a group of vessels containing a simple cup 74. Gravitation, piston pressure and suction can be used to move the immersion liquid in and out of the goggles.

Goggles 40 are sealed over the eye of the subject to avoid leakage of filler substance 22. Sealing may be enhanced when the sealing edges 76 touching the face are made from a soft material such as rubber, silicone, latex or similar materials. It is possible to add to the filler substance medication for muscle relaxation or pupil dilation, or nourishing matter, such as oxygen for the cornea. Thus the terms filler substance, immersion liquid and gel are being used interchangeably and using one of them can mean others as well.

The simplest goggles are clear cups worn over the eyes, in which case front lens 20 is a clear window of acceptable optical quality and the goggles are made from rigid or semi-rigid material such as plastics, rubber, silicone, latex and other such materials. The sealing edges 76 at the periphery of cup 21 can be made from the same material and is pressed against the face by retention system 60 containing straps 64, or by a helmet. The periphery can be made from rubber, latex, soft plastics and other similar materials. Pressure can be applied by retention system 60 or by holding the cup to the head directly, or by pressing the head against the cup 21, which is attached to a frame that may be a part of the ophthalmologic table or ophthalmologic instrument, or directly to the instrument itself.

In another embodiment, cup 21 or goggles 40 or parts thereof are manufactured from a degradable material.

In another embodiment, cup 21 or goggles 40 or parts thereof are manufactured from a non-degradable material, which can be disinfected and used more than once.

It may be wise to avoid multiple usages of the same goggles on different subjects. In order to make sure no multiple-use occurs, the goggles or parts thereof can be made from a material that is sensitive to disinfectants or to reopening or refilling or draining of the goggles. Alternatively is can be made from materials that degrade over time or under influence of chemicals or disinfectants—all in order to ensure single use. On the other hand, if one desires using the same goggles on the same subject over and over again care should be taken not to manufacture the device from such degradable materials.

In many cases, however, focus differences between subjects and usage of different optical system 50 requires that allowance be made for focus adjustment. This can be done by having several goggles, each with different lens 20 powers.

Alternatively, the sides of cups 21 can be made of semi-rigid material that can be inflated or deflated slightly, enabling focus changes as the distance of the front rigid lens correspondingly changes with respect to the eye. It can be made from a group of materials containing rubber, latex, silicone, and soft plastics.

In an alternative embodiment, the sides of cup 21 can be folded in the shape of a bellows (or accordion), also allowing adjustment by pressure changes or for different eye depth between subjects. Inside pressure can be varied by an external pump, such as a soft filling bag 72 or a hard vessel 51 which can be made to include a pump (see FIG. 6).

Yet another embodiment models comprises firm cup 21 sides that allow adjustment of the lens distance from the eye by pushing or pulling on it and sliding it in and out of the side walls without leak. Rotation of the lens 20 to align its optical axes can be achieved by movement of cup 21 or the entire goggles 40 against the eyes. Alternatively, this adjustment in height, distance from nose, eye depth, and tilt of the lens 20 can be relegated to a positioning mechanism 28. This mechanism or adjustment section allows mutual movement and rotation between the lens 20 and the eyecup 21 or goggles or mask 40. This mechanism can include three-directional and two angular stages as is well known to those trained in the art.

An alternative embodiment comprises a ball and socket mechanism with the ball having a bead shape for light passage and holding the lens across the light path. The bead with the lens inside can be rotated against the rest of the goggles until the its optical axis is aligned with the eye as required. The lateral direction movement can also be achieved by two eccentric cylinders.

An alternative embodiment enables adjustment of the eye-lens distance by a mechanism such as a screw or a piston with respect to the rest of the goggles.

An alternative embodiment enables modification of the shape or curvature of the lens by tightening a ring around the rim of the lens, thus changing the focus. In this case the lens is flexible enough to change its surfaces and achieve the necessary adjustment.

Yet another way of focus adjustment is by adjustment of the refractive index by changing the filler substance 22 for another substance with a different index, or a mixture of the substances, or by changing the temperature or pressure of substance 22 to change its refractive index, or any method or combination of methods to vary the refractive index.

Suction for reduction of the internal pressure can be used for reduction of the distance between the lens and the eye. Pressure can also be varied in conjunction with inflatable cavities created by additional membranes, instead of, or in parallel to the lens, so as to change the total optical power of the goggles, as described by Treisman et al, in U.S. Pat. No. 4,890,903, "SUSPENSION SYSTEM FOR A FLEXIBLE OPTICAL MEMBRANE" and Silver in U.S. Pat. No. 6,618,208, "VARIABLE FOCUS OPTICAL DEVICES".

In addition, it is possible to make some or all position adjustments for a particular subject externally, in an optical system which sends or receives the light from the eye, where such an optical system can also be simple spectacles, but also a much more complicated device such as (but not limited to) a laser scanner or a slit lamp, ophthalmoscope or optical coherence tomography device. Adjustment in any, part, or all of the above methods can be manual or mechanical and/or automated.

A more complex adjustment is for astigmatism. This can be corrected outside the goggles by cylindrical lenses or more complex systems, such as a combination of two cylindrical lenses with the angle between them adjusted for minimal focus point, as is known to those trained in the art. Alternatively, they can be corrected by directional pressure on the perimeter of the lenses of the goggles in specific orientations. Here the flexibility of the lenses allows their distortion in the required manner. Again, this can be manual or mechanical and/or automated.

The simplest procedure for any adjustment is by observation of light focused on the retina or in an external image and its reduction to a smaller spot size. The result of the adjustment is a sharper image, whereas a more blurry image indicates adjustment in the wrong direction. It is also possible to project light from one or more sources, such as infra-red light emitting diodes, and align their reflection from the eye with that of lens 20. This alignment can be visual or using a camera or other sensors. Other procedures can be through wave front sensing or other means, including subjective or objective response from the subject. This feedback mechanism can be manual, automated, or a combination of both.

After adjustment for focus and astigmatism as described above, the other main aberrations of the eye are spherical and chromatic. These can change with accommodation, age, and other parameters. On top of these aberrations, there are higher order aberrations, which are more specific to different subjects.

Lens 20 can be optimized for minimal spherical and chromatic errors by utilizing one of many available computerized lens design programs and modifying the shapes of the surfaces of the lenses, their numbers, and their material. Even the simplest spherical surfaces for the lens improve significantly spherical aberrations as compared to the average eye.

Lens 20 can be an optical system containing components from the group of a single lenses, doublets, triplets, diffractive lenses, mirrors, filters, stops, or even more complex optics. Conical, aspheric surfaces, or those parameterized in any other way, on its external side, internal side, or both can improve the spot quality even further and over a wider field of view. For monochromatic purposes, such as for laser surgery or narrow-band imaging, some or all the lens surfaces can be diffractive. Diffractive surfaces or diffractive lenses also allow reduction of chromatic aberrations in polychromatic imaging.

Care must be taken during design and optimization to minimize reflections from one or more of the surfaces of lens 20. This is because it might be difficult to separate it from light coming from inside the eye. Proper anti-reflection coating on the offending surfaces can solve the problem as well. Weak reflections from other ocular surfaces such as the cornea and crystalline lens (Purkinje reflections) might also be mistaken for light returning from the retina. These reflections can be separated or blocked during the lens design and optimization process, as is well known to those skilled in the art.

The diameter of lens 20 is mainly set by two parameters: its distance from the focus, and the diameter of the ocular iris. For example, if one focuses on the retina, light beams to or from the retina travel in essentially straight lines to the external lens, and the optical pupil is the ocular pupil, the iris of the eye. Any lens diameter, which will not block this cone of light, will be acceptable. To gain maximum resolution the iris is usually dilated in ophthalmic treatment to its maximal aperture, nearly eight millimeters. The cone of light from a single retinal point can be extended for a wider field of view of a larger portion of the retina.

With a longer optical path between goggles and retina, chromatic aberration is stronger as compared with the bare eye. If necessary it can be corrected by external optics and not only in the goggles. Diffractive optics can be incorporated into the system to have a better quality of the polychromatic image. Alternatively, a narrow-band filter can reduce significantly the chromatic aberration at the price of lost intensity. The extreme case is a laser beam where the chromatic error does not disturb at all because of the very narrow band width.

Figure 4:
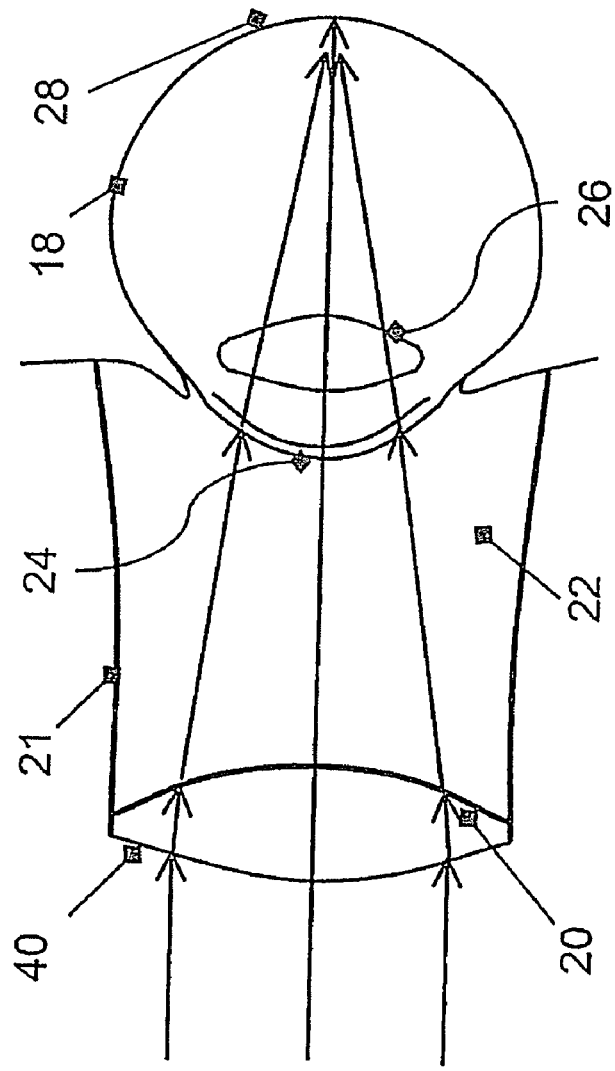
FIG. 4 is a schematic sectional view of an exemplary goggle by which light, possibly from a laser, is sharply focusing on the retina in accordance with a preferred embodiment of the present invention.

FIG. 4 is a side view generalized schematic illustration of an exemplary goggle in accordance with a preferred embodiment of the present invention. All distances are given in millimetres (mm). The diameter of the entering beam of light is limited to 8 mm at the pupil position. The biconvex lens 20 is made of the common glass of BK7, and is placed at 17 mm from cornea 24, further from most eye lash positions. Its diameter is 22 mm and its thickness is 6 mm, thus weighing only a few grams, a small addition to the weigh of the goggle and filler substance 22, which in this exemplary implementation is water. The front surface of lens 20 has a radius of curvature of 28.2 mm and conic constant of −1, and the second surface has a radius of curvature of −22.8 mm and conic constant of −0.39. This design minimizes the longitudinal aberration at the retina, and indeed the maximum wave front error is one fiftieth of a wave (at 0.55 micrometers). Very similar results can easily be obtained with other lens materials, such as glass or plastic. For example, with polycarbonate (refractive index 1.59) of the same thickness of 6 mm, the path in water is 24.6 mm; the front surface has 35.7 mm curvature and conic −1, the second surface curvature of −39.4 mm and conic 1. The wave front maximum deviation is 0.024 waves. The model of the eye was taken from H.-L. Liou and N. A. Brennan, "Anatomically accurate, finite model eye for optical modeling", Journal of the Optical Society of America A Vol. 14, 1684-95, 1997. Similar results are obtained from other models.

The high quality of the retinal image, obtained so simply, shows that indeed the combination of an optical front surface (as opposed to the biological cornea), combined with the few parameters available here, is already enough to reduce the aberrations of the natural perfect eye from the model. As can be seen from FIG. 4, the major refraction occurs at the front surface, with secondary refractions at the two fluid surfaces. That is enough to reduce significantly the spherical aberration of the naked, perfect, model eye. Higher term corneal aberrations are reduced by a factor of (1-1.37)/(1.34-1.37)=12.3, the ratio being of the refractive index change from air to cornea compared to the change from water to cornea. This is as if the common peak-to-valley fluctuations in the retinal surface and of the tear film drop from six micrometers to half a micrometer. The variability of the tear film is not felt any more, leading to a much more stable focal point, or alternatively to better imaging. When the water is replaced by a substance whose refractive index is even closer to that of the cornea, the aberrations are further reduced until they disappear at exact index match.

Figure 5A:
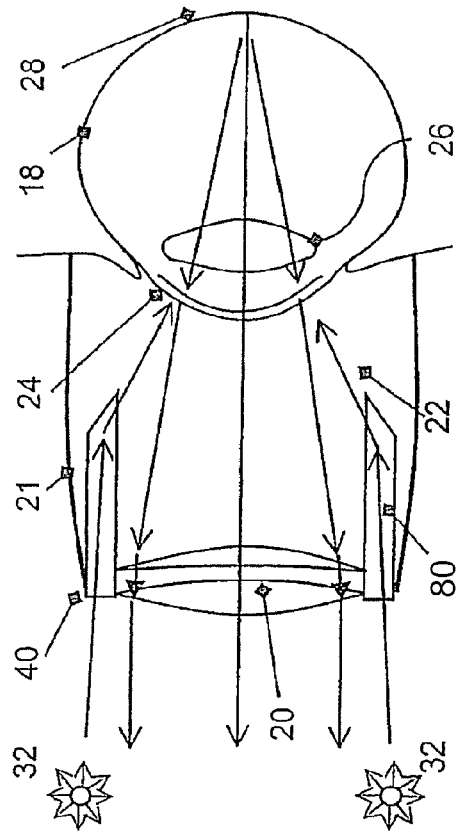
FIG. 5a is a schematic sectional view of a goggle according to a preferred embodiment of the present invention holding a more complicated lens system, and a peripheral light guide allowing ocular illumination without reflections from the lens system.
Figure 5C:
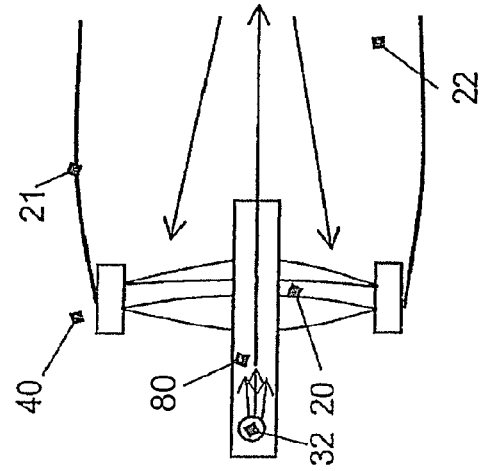
FIG. 5c is a sectional view of a goggle where the light guide is central to the lens system, holding also an optional light source for ocular illumination.
Figure 5B:
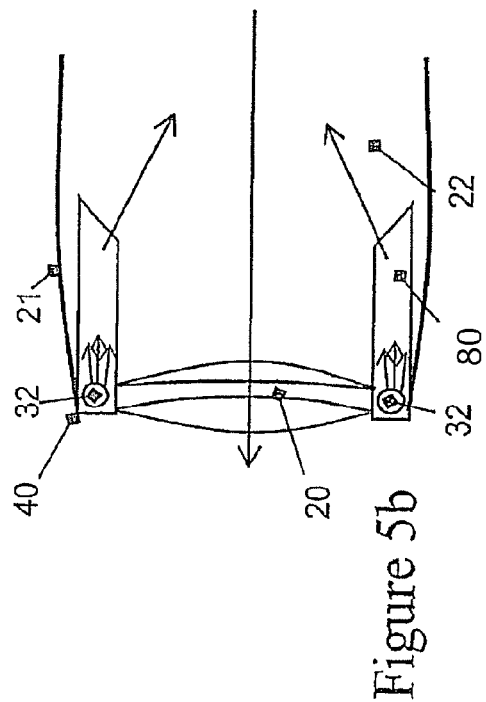
FIG. 5b is a sectional view of a goggle where a peripheral light guide holds also a light source for ocular illumination.

In this example a singlet lens was optimized. As is usual in optical design, a more sophisticated doublet or triplet has a much better quality. The optical system 50 can also have more elements, with air or fluid between them, the spacing being constant or variable, as shown in FIGS. 5a-5c. This internal adjustment can be for better image quality, but also for fine focusing, for obtaining a large field of view, for higher magnification, for concentrating on shallower or deeper parts of the eye, or for other targets and designs, as is well known to those skilled in the art. Experimenting with a well designed air-spaced doublet, the subjective image quality was indeed found to have improved.

Both optimization and utilization of the filled goggles are performed with light sources external to the eye. The eye is illuminated with sources from a group containing natural sources, incandescent sources, sources using heated filaments, narrow line lamps such as sodium or sodium, arc lamps, light-emitting and super-luminescent diodes, lasers of wide variety, and other sources and combinations thereof. In all applications and utilizations some of the light can be scattered back, for the ophthalmologist, researcher or other medical professional to measure its qualities. Hence both optimization and embodiments include these and other light sources, filtered or not. The light can be a continuous beam, single pulses or repetitive flashes, having periodic or aperiodic intensity variations, variable wave length, changing polarization, or combinations of these.

In another embodiment, the light illuminating the retina is not arriving through lens 20. In one option, the mechanism holding lens 20 to goggles 40 is transparent, serving as a window or a light guide. Light from a source 32 as described above, external to mounting elements 78 or 80 in FIGS. 5a, 5b, 5c and 6, passes through. Spurious reflections are avoided by separation of light paths into and out of the eye, as is made manifest by FIGS. 5a, 5b and 5c. The light guide can be a different unit from mounting elements 78 or 80, and can be in near contact with the sclera. In this case, scattered illumination from the sclera arrives inside the whole eye. In FIGS. 5a and 5b the light enters through a cylinder around the lens, coming from the outside (FIG. 5a) or from inside the cylinder itself (FIG. 5b). In FIG. 5c the light enters from the center of the field, and it can originate inside the light guide as shown or from the outside, similar to FIG. 5a.

Detection of the light can also be done in various ways, from direct eye view of light returned from inside the goggles, through film cameras, linear and rectangular charged coupled devices (CCDs) and CMOS cameras, arrays or single photodiodes, avalanche photodiodes and photomultipliers. Inclusion of optical and other components, such as mirrors, lenses, filters including also gratings or prisms, fibres or light guides, bean-splitters, and the like, between the sources, eyes and detectors, is also possible. Such detectors can also be included in the ocular measurement group of devices holding among others retinal cameras and scanners, slit lamps, ocular microscopes, scanning lasers and coherence sensors.

A combination of other sources such as acoustic, electromagnetic or radiative, and their detectors in conjunction with the goggles is also construed as application of the goggles as described in this disclosure. As described above, there are goggles for acoustic measurements of the eye, as well as newer probing methods such as PET or MRI, or for administration of medication or therapeutic treatment. Inclusion of the lens system as described here will allow both viewing by the subjects and examining their eyes optically if necessary.

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

The invention claimed is:

1. A device for improved vision into or out of at least one eye of a subject, the device comprising:
   at least one enclosing vessel for holding at least one lens in front of said at least one eye and for holding a substance whose refractive index is matched to the refractive index of the cornea of said at least one eye,
   wherein the vessel is adapted to seal the substance to the face of the subject around said at least one eye;
   thereby allowing focusing into or out of said at least one eye.

2. The device of claim 1, provided with at least one strap for restraining the device on the face of the subject.

3. The device of claim 1, wherein said at least one enclosing vessel comprises two vessels, each vessel provided with a lens.

4. The device of claim 1, incorporated in a helmet provided with at least one restraining strap.

5. The device of claim 1, provided with an adapter for attaching the device to a separate device.

6. The device of claim 1, wherein the optical properties of the lens are variable.

7. The device of claim 1, further provided with at least one external optical element adapted to be placed in front of the device.

8. The device of claim 1, wherein said at least one lens is selected from a group of optical systems consisting of a single lens, a doublet, a triplet, a diffractive lens, a variable index lens, a compound lens, flexible lens, lens with anti-reflection coating, mirrors, or a combination thereof.

9. The device of claim 1, provided with an adjustment mechanism for orienting and displacing said at least one lens.

10. The device of claim 1, wherein the vessel has at least one opening in it through which the substance can be changed or modified or added or removed.

11. The device of claim 1, further provided with at least one transparent partition so as to allow the vessel to separately hold substances of different optical characteristics.

12. The device of claim 1, further provided with a light source for illuminating said at least one eye.

13. The device of claim 1, provided with at least one wave guide for guiding light into said at least one eye.

14. The device of claim 1, wherein the vessel is flexible.

15. A method for improving vision into or out of at least one eye of a subject, the method comprising:
- providing a device comprising at least one enclosing vessel for holding at least one lens in front of said at least one eye;
- providing within the vessel at least one substance whose refractive index is matched to the refractive index of the cornea of said at least one eye,
- sealing the vessel to the face of the subject around said at least one eye;
- thereby allowing focusing into or out of said at least one eye.

16. The method of claim 15, further comprising strapping the vessel to the face of the subject.

17. The method of claim 15, further comprising displacing or tilting said at least one lens.

18. The method of claim 15, further comprising placing one or more transparent substances separately in the vessel.

19. The method of claim 15, wherein the vessel is flexible, further comprising changing pressure within the vessel to change at least one optical property of the device.

20. The method of claim 15, wherein matching the refractive index of the substance to the refractive index of the cornea comprises partially or fully replacing or mixing the substance within the vessel with another substance of different optical properties or for nutritional or medical purposes.

21. The method of claim 15, wherein said at least one lens is flexible, further comprising applying pressure on or around said at least one lens to change its optical properties.

22. The method of claim 15, used in conjunction with ocular measurements or imaging.

23. The method of claim 15, used in conjunction with ocular surgery or procedure.

24. The method of claim 15, further comprising correcting aberrations using an adaptive optics system, the system comprising at least one component from a group of components consisting of a wave front sensor, a wave front modulator, and a servo controller.

* * * * *